United States Patent
Okuhara et al.

(10) Patent No.: US 7,115,782 B2
(45) Date of Patent: Oct. 3, 2006

(54) PROCESS FOR PRODUCING AROMATIC COMPOUNDS BY FRIEDEL-CRAFTS REACTION

(75) Inventors: Toshio Okuhara, Sapporo (JP); Tetsuo Nakajo, Oita (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/516,454

(22) PCT Filed: May 15, 2003

(86) PCT No.: PCT/JP03/06078

§ 371 (c)(1),
(2), (4) Date: Dec. 3, 2004

(87) PCT Pub. No.: WO03/101925

PCT Pub. Date: Dec. 11, 2003

(65) Prior Publication Data

US 2005/0222457 A1    Oct. 6, 2005

Related U.S. Application Data

(60) Provisional application No. 60/386,744, filed on Jun. 10, 2002.

(30) Foreign Application Priority Data

Jun. 3, 2002  (JP) .............................. 2002-161164

(51) Int. Cl.
 C07C 45/00  (2006.01)
 C07C 51/00  (2006.01)
(52) U.S. Cl. ..................... 568/315; 568/322; 568/328; 562/406; 562/497

(58) Field of Classification Search ..................... None
See application file for complete search history.

(56) References Cited

U.S. PATENT DOCUMENTS 2,587,540 A    2/1952   Shaver
6,372,938 B1   4/2002   Burzynski et al.

FOREIGN PATENT DOCUMENTS

DE    2814129 A1    10/1979

OTHER PUBLICATIONS

Mao, Jianxin et al, "Alkylation-Acylationof Aromatics with γ-Butyrolactone Catalyzed by Heteropolyacids Supported on Silica", Chemistry Letters 2002, (11), 1104-1105, XP008022158.
Izumi, Yusuke, et al, "Silica-Supported Heteropoly Acid Catalyst for Liquid-Phase Friedel-Crafts Reactions", Bull. Chem. Soc. Jpn., 62, 2159-2162(1989), XP002254789.
"Friedel-Crafts-type acylation by insoluble heteropoly acid catalysts", TAGAWA, Tomohiko, et al.., Chemical Abstracts, vol. 124, No. 15, Apr. 9, 1996, Columbus, Ohio, XP000663136.
International Search Report for PCT/JP03/06078 dated Sep. 29, 2003.
Patent Abstracts of Japan, vol. 017, No. 274 (C-1064), May 27, 1993 &.
JP 05 009135 A (Nippon Shokubai Co. Ltd), Jul. 19, 1993.
Izumi et al. "Acidic Alkali Metal Salts and Ammonium Salts of Keggin-type Heteropolyacids as Efficient Solid Acid Catalysts for Liquid-phase Friedel-Crafts Reactions." Chemistry Letters, 1992, pp. 1987-1990.

*Primary Examiner*—Sikarl A. Witherspoon
(74) *Attorney, Agent, or Firm*—Sughrue Mion, PLLC

(57) ABSTRACT

There is provided a process for producing an aromatic compound by Friedel-Crafts reaction product, which comprises reacting an aromatic compound with an ester compound in the presence of a heteropolyacid-containing solid acid catalyst.

14 Claims, No Drawings

PROCESS FOR PRODUCING AROMATIC COMPOUNDS BY FRIEDEL-CRAFTS REACTION

CROSS-REFERENCES TO RELATED APPLICATIONS

This application is a 371 of PCT/JP03/06078 filed May 15, 2003 and published as WO 03/101925 on Dec. 11, 2003.

The application is an application filed under 35 U.S.C. §111 (a) claiming pursuant to 35 U.S.C. §119 (e) of the filing date of Provisional Application 60/386,744 on Jun. 10, 2002, pursuant to 35 U.S.C. §111 (b).

FIELD OF THE INVENTION

The present invention relates to a process for producing aromatic ketones, aromatic carboxylic acids, aromatic alcohols, and alkylated or alkenylated aromatics by the Friedel-Crafts reaction of an aromatic compound and an ester compound in the presence of a heteropolyacid-containing solid acid catalyst. Aromatic compounds by Friedel-Crafts reaction such as aromatic ketones, aromatic carboxylic acids, aromatic alcohols, and alkylated or alkenylated aromatics are industrially useful compounds and are widely used as raw materials for medicaments, raw materials for pesticides, electronic materials, and raw materials for functional resins.

BACKGROUND OF THE INVENTION

Processes for producing Friedel-Crafts reaction products and catalysts thereof are described in many literatures. For example, Hendrickson, Cram, Hammond "ORGANIC CHEMISTRY" (third edition), page 668–683(1970) describes that an aromatic compound is alkylated or acylated by the Friedel-Crafts reaction. The literature includes an example in which alkyl halide, olefin, alcohol and p-toluenesulfonylated alkane are alkylated in the presence of aluminum chloride and concentrated sulfuric acid. It also describes that an aromatic compound is acylated by aluminum chloride, boron trifluoride, hydrogen fluoride, phosphoric acid and sulfuric acid using acid halide or acid anhydride as an acylating agent. It also describes that the Fries rearrangement proceeds by aluminum chloride and the Hoesch reaction proceeds by zinc chloride as a similar example of the Friedel-Crafts reaction in view of a reaction mechanism.

The processes of synthesizing indanone, which is useful as raw materials for medicaments, include, but are not limited to, a process wherein cinnamic acid is synthesized by the Perkin reaction of benzaldehyde and the resulting cinnamic acid is reduced with hydrogen to form phenylpropionic acid, which is further converted into indanone by the intramolecular acylation reaction, and a process as shown in the following reaction scheme 1, wherein acrylic acid is reacted with thionyl chloride to form acid chloride, and the resultant acid chloride is reacted with benzene in the presence of large amounts of aluminium chloride to prepare indanone.

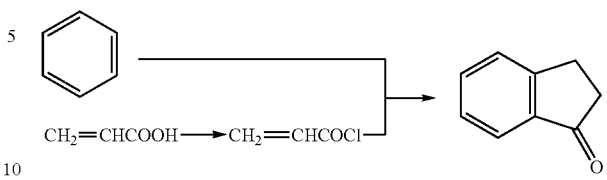

Reaction Scheme 1

As shown in the following reaction scheme 2, tetralone is obtained in the similar manner. For example, benzene is reacted with succinic anhydride using an aluminum chloride reagent to form a phenylketobutyric acid, which is reduced with hydrogen to obtain phenylbutyric acid, and then tetralone is obtained by intramolecular acylation of phenylbutyric acid using an aluminum chloride reagent.

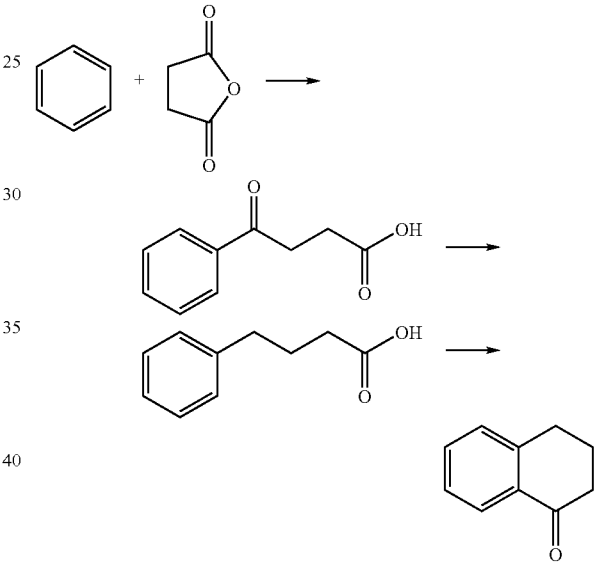

Reaction Scheme 2

All of the processes as mentioned above require a plurality of reaction steps and are complicated. In addition, aluminium chloride, thionyl chloride, acid chloride, and the like, are fuming, errosive, and poisonous, and therefore a care must be taken in handling these substances.

C. De Castro et al., J. Molecular Catal., 134, (1998) 215–222 has reported that an indanone derivative is produced from crotonic acid and m-xylene as raw materials using a 60% phosphorus-tungsten-carrying catalyst. However, TON (the number of products per number of catalytic active sites) is very low such as 3.5 and an improvement is required in view of the synthesis.

Similarly, as the process of synthesizing an alkylcarboxylic acid containing trimethylbenzene, there is proposed a process of synthesizing the alkylcarboxylic acid by converting aldehyde of trimethylbenzene into ketocarboxylic acid by means of the Perkin reaction and reducing the resulting ketocarboxylic acid with hydrogen.

E. F. Kozhevnikova et al., Chem. Comm, 2002, (11), 1178–1179 has reported a similar reaction by means of the Fries rearrangement reaction.

As described in the prior art, zinc chloride including aluminum chloride is required as a reagent for promoting the Friedel-Crafts reaction and a polar solvent such as nitromethane or nitrobenzene is commonly used to dissolve the chloride. In addition to aluminum chloride, mineral acids such as boron trifluoride, hydrogen fluoride, phosphoric acid and sulfuric acid as well as trifluorosulfonic acid have been used.

These reagents often caused a problem in the post-treatment steps such as purification and separation after the reaction. For example, upon separation and recovering when using aluminum chloride, aluminum chloride is hydrolyzed to produce a large amount of wastes. In case of recovering the product, it is often difficult to separate the aqueous layer and the organic layer of an aluminum chloride hydrolysis solution. Because of evolution of a large amount of a hydrochloric acid gas, the material of the reactor requires acid resistance and a high-quality material must be used.

Therefore, the present invention provides a means for solving many problems described above. By providing a process for producing an aromatic compound by Friedel-Crafts reaction by reacting an aromatic compound with an ester compound in the presence of a heteropolyacid-containing solid acid catalyst, it is made possible to provide an environmentally friendly and economical process, which replaces the reaction reagent by a catalyst, thereby to prevent production of a large amount of wastes, facilitates separation and recovering of the catalyst, and sometimes enables reuse of the catalyst and eliminates the use of a reactor made of a high-quality material.

As described above, a conventional process of synthesizing indanone, tetralone and alkane having a trimethylphenyl group requires a large number of the reaction processes and was inferior in economical efficiency taking account of equipment cost, labor cost, utilities cost and waste disposal cost. The process of C. De Castro et al. is an epoch-making process for synthesizing indanone, but is insufficient in TON which exhibits catalytic performances, and the process does not describe sufficient information with respect to separation and reuse of the catalyst.

SUMMARY OF THE INVENTION

To achieve the object described above, the present inventors have intensively studied and found that the objective aromatic compound by Friedel-Crafts reaction can be obtained with high yield by reacting an aromatic compound with an ester compound in the presence of a heteropolyacid-containing solid acid catalyst, and thus they have completed the present invention including:

[1] A process for producing an aromatic compound by Friedel-Crafts reaction product, which comprises reacting an aromatic compound with an ester compound in the presence of a heteropolyacid-containing solid acid catalyst;

[2] The process according to [1], wherein the heteropolyacid-containing solid acid catalyst is a solid acid catalyst comprising a carrier and a heteropolyacid carried on the carrier;

[3] The process according to [1] or [2], wherein a central atom of the heteropolyacid is selected from the group consisting of P, Si, B, Ge and As and a coordinating atom comprises at least one of Mo and W;

[4] The process according to [1] or [2], wherein a central atom of the heteropolyacid is selected from the group consisting of Si and Ge and a coordinating atom comprises at least one of Mo and W;

[5] The process according to [1], wherein an amount of the heteropolyacid carried in the heteropolyacid-containing solid acid catalyst is 50% by weight or less;

[6] The process according to [1], wherein an amount of the heteropolyacid carried in the heteropolyacid-containing solid acid catalyst is 30% by weight or less;

[7] The process according to [2], wherein a relative surface area of the carrier supporting the heteropolyacid is 20 $m^2/g$ or more;

[8] The process according to [2], wherein the carrier carrying the heteropolyacid has a purity of 98% or higher;

[9] The process according to [1], wherein the ester compound comprises lactones;

[10] The process according to [1], wherein the aromatic compound by Friedel-Crafts reaction comprises aromatic ketones, aromatic carboxylic acids, aromatic alcohols, or alkylated or alkenylated aromatics;

[11] The process according to [10], wherein the aromatic compound by Friedel-Crafts reaction is aromatic ketones or aromatic carboxylic acids;

[12] The process according to [11], wherein the aromatic compound by Friedel-Crafts is aromatic ketones;

[13] The process according to [1], wherein the Friedel-Crafts reaction product is cyclized ketones;

[14] The process according to [1], comprising the step of reusing the heteropolyacid-containing solid acid catalyst after separating and recovering it;

[15] The process according to [14], wherein the catalyst is regenerated in the step of reusing the heteropolyacid-containing solid acid catalyst after separating and recovering it; and

[16] An aromatic compound by Friedel-Crafts reaction, produced by the production process of any one of [1] to [15].

DETAILED DESCRIPTION OF THE INVENTION

The present invention will now be described.

The aromatic compound in the present invention as a raw material (hereinafter also referred to as simply "aromatic compound") is an extended aromatic compound which is composed of an aromatic ring or heterocycle having at least one moiety which undergoes the Friedel-Crafts reaction, and also includes a hydrocarbon-type aromatic compound such as benzene or naphthalene, a non-benzene-type aromatic compound such as cyclopentadiene or cycloheptatriene, and a heterocyclic compound such as pyridine, pyrrole or tetrahydrofuran. Those having a substituent such as alkyl group, hydroxyl group, amino group, nitro group, alkoxy group, acetyl group or halogen are also included.

The aromatic compound in the present invention will now be described.

Typical examples of the hydrocarbon-type aromatic compound such as benzene or naphthalene in the present invention include benzene, naphthalene, anthracene, phenanthrene, diphenylmethane, biphenyl, biphenyl ether and fluorene. The non-benzene-type aromatic compound also includes cyclopentadiene, cycloheptatriene, and a compound condensed thereto. Typical examples thereof include indan. A heterocyclic compound such as pyridine, pyrrole, tetrahydrofuran or thiophene can also be listed.

Examples of the substituent bonded to an aromatic compound skeleton in the present invention include, but are not limited to, alkyl group, hydroxyl group, amino group, nitro group, alkoxy group, acetyl group, halogen, and group having halogen.

Examples of the aromatic compound having an alkyl substituent include compound having an alkyl substituent on the benzene ring, such as toluene, o-xylene, m-xylene, p-xylene, mesitylene, 1,2,3-trimethylbenzene, 1,2,4-trimethylbenzene, 1,2,3,4-tetramethylbenzene, 1,2,3,5-tetramethylbenzene, 1,2,4,5-tetramethylbenzene, ethylbenzene, n-propylbenzene, cumene, n-butylbenzene, isobutylbenzene, or t-butylbenzene; compound having a methyl group on the naphthalene ring, such as 1-methylnaphthalene, 2-methylnaphthalene, 1,2-dimethylnaphthalene, 2,3-dimethylnaphthalene, 1,3-dimethylnaphthalene, 1,4-dimethylnaphthalene, 2,6-dimethylnaphthalene, 1,2,3-trimethylnaphthalene, 1,6,7-trimethylnaphthalene, 2,6,7-trimethylnaphthalene, 1,4,5-trimethylnaphthalene, 1,4,6-trimethylnaphthalene, 2,3,5-trimethylnaphthalene, 2,3,6-trimethylnaphthalene, 1,4,5,8-tetramethylnaphthalene, or 2,3,6,7-tetramethylnaphthalene; compound having an alkyl substituent on the anthracene ring; compound having an alkyl substituent on the phenanthrene ring; compound having an alkyl substituent on the benzene ring of diphenylmethane; compound having an alkyl substituent on the benzene ring of biphenyl; compound having an alkyl substituent on the benzene ring of biphenyl ether; compound having an alkyl substituent on the fluorene ring; and compound having an alkyl substituent on the indene ring.

A compound having a halogen substituent, an alkoxy substituent, a hydroxyl group, an amino group, a nitro group or an acetyl group on the aromatic ring is also included in the aromatic compound having a substituent. Examples thereof include chlorobenzene, chlorotoluenes, chloroxylenes, bromotoluenes, bromoxylenes, anisole, veratole, methoxytoluenes, methoxyxylenes, phenols, anilines, nitrobenzenes, and methyl phenyl ketones.

Examples of the non-benzene-type aromatic compound include cyclopentadiene, methylcyclopentadiene, dimethylcyclopentadiene, cycloheptatriene, methylcycloheptatriene, and a compound condensed thereto, such as indan or methylindan.

The heterocyclic compound in the present invention is a compound having a ring formed of two or more kinds of atoms. Examples thereof include pyrrole, furan, thiophene, imidazole, oxazole, thiazole, pyrazole, 3-pyrrolinepyrrolidine, pyridine, pyrimidine, purine, quinoline, isoquinoline, carbazole, indole, and benzofuran. The heterocyclic compound having a substituent may have an alkyl substituent, a halogen substituent, an alkoxy substituent, a hydroxyl group, an amino group, a nitro group or an acetyl group on the ring of the heterocyclic compound. Examples thereof include methylpyrrole, ethylpyrrole, propylpyrrole, methylfuran, ethylfuran, propylfuran, methylthiophene, ethylthiophene, propylthiophene, methylimidazole, ethylimidazole, propylimidazole, methyloxazole, ethyloxazole, propyloxazole, methylthiazole, ethylthiazole, propylthiazole, methylpyrazole, ethylpyrazole, propylpyrazole, methyl-3-pyrrolinepyrrolidine, ethyl-3-pyrrolinepyrrolidine, propyl-3-pyrrolinepyrrolidine, picoline, ethylpyridine, propylpyridine, methylpyrimidine, ethylpyrimidine, propylpyrimidine, methylpurine, ethylpurine, propylpurine, methylquinoline, ethylquinoline, propylquinoline, methylisoquinoline, ethylisoquinoline, propylisoquinoline, methylcarbazole, ethylcarbazole, propylcarbazole, methylindole, ethylindole, propylindole, methylbenzofuran, ethylbenzofuran, propylbenzofuran, methoxyfuran, furan chloride, benzofuran chloride, benzothiophene chloride, acetoaminopyrrole, nitropyrrole, nitrobenzofuran, acetoxyfuran, acetoxypyrrole, nitroindole, dimethylaminoindole, dimethylindole, N-acyldimethylindole, methylbenzofuran chloride, thiophenoxyfuran, and phenoxypyrrole.

The aromatic compound in the present invention is preferably a hydrocarbon-type aromatic compound such as benzene or naphthalene, or a non-benzene-type aromatic compound. More preferably, it is a hydrocarbon-type aromatic compound having an alkyl substituent, such as benzene or naphthalene and examples thereof include toluene, xylene, trimethylbenzene, and methylnaphthalene. An alkyl benzene-type hydrocarbon-type aromatic compound is more preferred.

These aromatic compounds can be used as such as far as they are general industrial grade compounds. Preferably, these aromatic compounds are used after purifying so as to meet the standard of the resulting product. The purification process may be any processes, which are well known to a person with an ordinary skill in the art, such as distillation, recrystallization, rinsing, filtration with dissolving, and removal with adsorption.

The ester compound in the present invention is a compound having an ester group (—COO—) and refers to lactones as an intramolecularly cyclized ester, an aliphatic or aromatic ester, or a carbonate ester (—OCOO—). Particularly, lactones are preferred. Examples thereof include β-propiolactone, γ-butyrolactone, δ-valerolactone, ε-caprolactone, γ-valerolactone, γ-caprolactone, γ-caprylolactone, γ-laurolactone, crotolactone, α-angelicalactone, β-angelicalactone, δ-caprolactone, tetronic acid, α-pyrone, β-pyrone, phthalide, coumarin, and macrocyclic lactone.

The aromatic compound by Friedel-Crafts reaction produced in the present invention (hereinafter also referred to as "Friedel-Crafts reaction product) includes aromatic ketones, aromatic carboxylic acids, aromatic alcohols, and alkylated or alkenylated aromatics. The present invention is suitable for use in the process for producing aromatic ketones and aromatic carboxylic acids as the Friedel-Crafts reaction product. The present invention is suitable more preferably for use in the process for producing aromatic ketones as the Friedel-Crafts reaction product. The present invention is suitable for use in the process for producing clyclized ketones as the Friedel-Crafts reaction product among the aromatic ketones. The present invention is most suitable for used in the process for producing indanones and tetralones.

According to the process of the invention, as shown in the following reaction scheme 3, it is made possible to produce tetralone and 3-methylindanone in one step by the Friedel-Crafts reaction between benzene and γ-butyrolactone.

Reaction Scheme 3

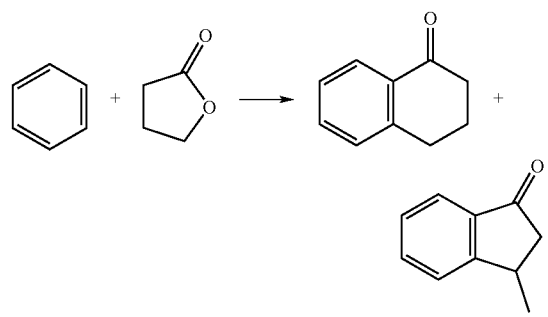

The solvent used in the Friedel-Crafts reaction of the present invention may be an industrial grade solvent which is not a special high-purity product. An aromatic compound as a raw material of the Friedel-Crafts reaction can be used as the solvent. In case the aromatic compound as the raw material of the Friedel-Crafts reaction and the solvent are separately used, an aromatic compound for the solvent having reactivity lower than that of the aromatic compound for the raw material must be used.

The catalyst used in the present invention will now be described.

The catalyst in the present invention is a heteropolyacid-containing solid acid catalyst. The heteropolyacid is defined as a generic name of an acid produced by condensing two or more kinds of inorganic oxyacids (Kagaku Sosetsu, "Design of Catalysts", No. 34, 116–141 (1982), Gakkai Shuppan Center). Examples of the heteropolyacid-containing solid acid catalyst include catalyst made only of the heteropolyacid, heteropolyacid-containing catalyst comprising a carrier and a mixture with the heteropolyacid or the heteropolyacid carried on the carrier, and catalyst containing the heteropolyacid entrapped therein. Among these catalysts, a catalyst comprising a carrier and the heteropolyacid carried on the carrier is preferred.

The heteropolyacid in the present invention is preferably a heteropolyacid wherein a central atom comprises P, Si, B, Ge or As and a coordinating atom comprises Mo or W, or a mixture thereof. Specific examples thereof include $[PMo_{12}O_{40}]^{3-}$, $[SiMo_{12}O_{40}]^{4-}$, $[GeMo_{12}O_{40}]^{4-}$, $[AsMo_{12}O_{40}]^{3-}$, $[PMo_{11}O_{39}]^{7-}$, $[AsMo_{11}O_{39}]^{7-}$, $[SiMo_{11}O_{39}]^{8-}$, $[GeMo_{11}O_{39}]^{8-}$, $[P_2Mo_{18}O_{62}]^{6-}$, $[As_2Mo_{18}O_{62}]^{6-}$, $[PW_{12}O_{40}]^{3-}$, $[SiW_{12}O_{40}]^{4-}$, $[GeW_{12}O_{40}]^{4-}$, $[AsW_{12}O_{40}]^{3-}$, $[PW_{11}O_{39}]^{7-}$, $[AsW_{11}O_{39}]^{7-}$, $[SiW_{11}O_{39}]^{8-}$, $[GeW_{11}O_{39}]^{8-}$, $[P_2W_{18}O_{62}]^{6-}$, and $[As_2W_{18}O_{62}]^{6-}$. Examples of the heteropolyacid wherein the coordinating atom comprises the mixture of Mo and W include $[SiW_1Mo_{11}O_{40}]^{4-}$, $[SiW_2Mo_{10}O_{40}]^{4-}$, $[SiW_3Mo_9O_{40}]^{4-}$, $[SiW_4Mo_8O_{40}]^{4-}$, and $[SiW_{11}Mo_1O_{40}]^{4-}$.

More preferred heteropolyacid is a heteropolyacid wherein the central atom comprises Si or Ge and the coordinating atom comprises Mo or W, or a mixture thereof.

The counter cation is preferably proton, ammonium salt or alkali metal salt.

The heteropolyacid in the present invention can be synthesized by a process well known in the art. Specifically, the heteropolyacid can be obtained by heating an aqueous acidic solution (pH: about 1 to 2) containing a salt of molybdic acid or tungstic acid and simple oxyacid of a hetero atom or a salt thereof. A commercially available reagent may be used as such.

Examples of the carrier used in the present invention include silica, activated carbon, and diatomaceous earth ("soil produced as a result of accumulation of husk of diatom, pure silicic acid husk comprising 94% $SiO_2$ and 6% $H_2O$", Iwanami Rikagaku Jiten, fifth edition, page 405 (1998)). Among these carriers, silica and activated carbon are preferred and high-purity silica is more preferred.

The carrier having higher purity is preferred. The purity of the carrier is preferably 96% or higher, and more preferably 98% or higher. When the carrier contains a component capable of decomposing the heteropolyacid, sufficient performances can not be exhibited. Alkali metal oxide, alkali earth metal oxide, alumina, gallium oxide and indium oxide are unfavorable impurities. The purity of the carrier is calculated while components other than $SiO_2$ as a main component being considered as impurities in case of silica and diatomaceous earth, or components other than C being considered as impurities in case of activated carbon.

The carrier having smaller particle diameter exhibits catalytic performances more easily. However, in deciding the particle diameter, it is also necessary to take into account balance between the catalytic performance and separability of the catalyst from a reaction solution during sedimentation or filtration. In general, the carrier is not only in the form of primary particles, but also in the form of an aggregate or floc. With respect to the particle size, the carrier including the aggregate preferably has a weight-average particle diameter of 10 μm or more, more preferably 50 μm or more, and still more preferably 200 μm or more.

The particle size distribution is preferably narrow to some extent in the preparation of the catalyst. Since the carrier is likely to be formed into powders while stirring, the carrier preferably has sufficient mechanical strength.

The carrier is preferably a porous carrier including pores having a diameter of 1 nm or more. The narrower pore size distribution exhibits catalytic performances more easily after supporting. The pore volume is preferably 0.1 ml/g or more, and more preferably 0.2 ml/g or more.

The relative surface area of the carrier preferably 10 $m^2/g$ or more, and more preferably 20 $m^2/g$ or more. Silica and diatomaceous earth preferably has a relative surface area of 20 $m^2/g$ or more, while activated carbon preferably has a relative surface area of 500 $m^2/g$ or more. The relative surface area is a value as measured by a BET process using a nitrogen gas and the measuring process is described, for example, in "Shokubai Koza 3 (Catalyst Lecture 3), Characterization of Solid Catalyst", pages 204–5 (1985), Kodansha Scientific.

The carrier is preferably subjected to a pretreatment. Acid cleaning is preferably conducted when the carrier includes a large amount of impurities. When using silica, it is preferably sintered between 400° C. and 800° C.

As the process of carrying the heteropolyacid on the carrier, an impregnation process (comprising impregnating the whole carrier with a heteropolyacid solution according to the volume of the carrier) is generally used. A dipping process (comprising dipping the carrier in an excess amount of a heteropolyacid solution and swishing the heteropolyacid solution off, thereby carrying the heteropolyacid absorbed in the carrier) can also be used.

The amount (rate) of the heteropolyacid carried is calculated by the following equation.

Supporting amount=[(weight of heteropolyacid)/
((weight of heteropolyacid)+weight of carrier)]
*100

The heteropolyacid carrying amount is preferably 50% by weight or less, and more preferably 30% by weight or less. Too large carrying amount makes it impossible to sufficiently exhibit the function of the heteropolyacid, resulting in poor economy. Also too small carrying amount makes it impossible to sufficiently exhibit the function.

After carrying the heteropolyacid, the carrier is dried at the temperature at which the heteropolyacid is not decomposed. The temperature is preferably 300° C. or lower, and more preferably 280° C. or lower. The drying times may be preferably several times, and more preferably 4 hours or more. It is preferred to dry in a clean air flow.

The dried heteropolyacid-carrying catalyst is preferably stored in a dried state. The dried heteropolyacid-carrying catalyst is preferably removed from the dryer immediately after drying and then put in a sealed container covered with a desiccating agent so that the catalyst hardly absorbs moisture.

The heteropolyacid-carrying catalyst of the present invention is preferably activated before use in the Friedel-Crafts reaction. The catalyst may be activated by treating at the same temperature as the drying temperature for the same time. Although it depends on the storage method, performances of the catalyst are likely to be changed by re-adsorption of moisture during the storage. This is because, it is presumed that the catalyst returns to the state suited for the objective reaction in the present invention.

The process for producing a Friedel-Crafts reaction product by reacting an aromatic compound with an ester compound in the presence of the solid acid catalyst prepared by the above process will now be described.

A molar ratio of the ester compound to the aromatic compound is preferably from 1 to 400, more preferably from 3 to 300, and still more preferably from 5 to 200.

A molar ratio of the ester compound to the heteropolyacid-carrying solid acid catalyst is preferably 5:1 or less, and more preferably 10:1 or less.

The sequence of the aromatic compound, the ester group-containing compound, the catalyst and the solvent to be charged does not exerts a large influence on the reaction results. However, these components are preferably mixed and reacted before the temperature of the mixture raises to the reaction temperature. If possible, it is preferred to sufficiently mix them at room temperature.

Although the reaction temperature and the reaction pressure of the Friedel-Crafts reaction of the present invention vary because they are influenced by the kinds of the aromatic compound and the ester compound, the reaction temperature is preferably between 150° C. and 250° C. The reaction can be conducted at normal pressure, or under pressure or reduced pressure, but is preferably conducted under a pressure within a range from normal pressure to 500 kPa (gauge pressure).

The heating rate during the reaction is important. According to the kind of the ester compound, polymerization of the ester compound often occurs without conducting proper Friedel-Crafts reaction. The polymerization often occurs at the temperature lower than the temperature at which proper Friedel-Crafts reaction occurs. Therefore, it is preferred to raise to the desired reaction temperature by increasing the heating rate as high as possible.

The reaction time must be optimized by the molar ratio of the aromatic compound to the ester compound and the reaction conditions. For example, when the reaction is conducted for too long time, the valuable objective compound is sometimes decomposed. It is important to synthesize by optimizing the reaction conditions without being decomposed.

The reaction is preferably conducted in a reaction atmosphere after removing oxygen and moisture as much as possible. In case the reaction is conducted in an autoclave, the reaction is preferably initiated after the atmosphere in the autoclave is replaced by an inert gas (for example, nitrogen, argon, or helium).

Separation, recovering and reuse of the heteropolyacid-containing solid acid catalyst will now be described.

In case the catalyst sediments while standing after the completion of the reaction, the supernatant is drawn and the catalyst proceeds to the purification step of the product. The catalyst separated and recovered can also be reused as such. As a matter of course, in case of the catalyst which can not be separated, there can be used a separation process (for example, centrifugation, or filtration) which can be carried out by a person with an ordinary skill in the art.

In the step of separating, recovering and reusing the heteropolyacid-containing solid acid catalyst, the process for producing the Friedel-Crafts reaction product including regeneration of the catalyst will now be described.

The catalyst regeneration process includes cleaning with an organic solvent. In this case, cleaning with heating is preferred. The cleaning solvent is preferably a solvent such as hydrocarbon-type hexane, heptane, or methylene chloride. After the filtration, the catalyst is sufficiently dried at about 100° C. Thereafter, the resulting catalyst can be used again as the catalyst.

A batch-wise reactor is used, commonly, and also a liquid-phase flow system or a catalyst fixed bed of the liquid-phase flow system can be used.

Although the material of the reactor varies depending on the kind of raw materials and reaction conditions, stainless steel and carbon steel are commonly used.

The following Examples illustrate the present invention in detail, but are not intended to limit the present invention.

EXAMPLES

Example 1

Silica-carried 10% Tungstosilicic Acid Catalyst, p-xylene

As a heteropolyacid, tungstosilicic acid (special grade chemical, pure chemistry: $SiO.12WO_3.26H_2O$) was used as such without being purified. Silica (Fuji Silicia Q-10, surface area: 270 $m^2/g$, pore diameter: about 10 nm, pore volume: 0.82 cc/g, impurities: Na=240 ppm, Al=65 ppm, Ca=130 ppm, Ti=100 ppm, total content of impurities=594 ppm, and therefore silica purity is 99.9% or higher) was used after firing in a muffle furnace at 500° C. for 5 hours.

The process for producing a catalyst will be described. 6.67 g of tungstosilicic acid was dissolved in 78 ml of pure water and 60 g of fired silica was impregnated with the resulting solution. After air drying, the impregnated silica was dried in a hot-air drying apparatus at 150° C. for 10 hours. The resulting catalyst is referred to as 10 wt % $HSiW/SiO_2$ catalyst.

In a 300 ml stainless steel autoclave equipped with a stirrer, 100 ml of p-xylene (799 mmol) and 1 ml of γ-butyrolactone (14.8 mmol) were charged and 3.20 g of the 10 wt % $HSiW/SiO_2$ catalyst (0.097 mmol-HSiW) was charged, and then the autoclave was capped. The autoclave was purged with an accumulated high-purity nitrogen gas and this operation was repeated 10 times. After confirming the absence of pressure loss, the gas was purged. To accelerate temperature raise, the autoclave was dipped in a previously heated oil bath and the reaction was initiated. The reaction was conducted at 200° C. for 5 hours. After the completion of the reaction, the supernatant was removed and then analyzed by an internal standard process using GC (FID, He carrier gas, 30mDB-1 column). After the reaction was conducted for 5 hours, the conversion ratio of γ-butyrolactone was 64.3%, the yield of 5,8-dimethyltetralone based on γ-butyrolactone was 39.9% (TON=15), and the yield of trimethylindanone was 2.6%.

Example 2

Reuse of Catalyst

Using the same reactor as in Example 1, 3.20 g of the 10 wt % $HSiW/SiO_2$ catalyst (0.097 mmol-HSiW) as the catalyst produced in Example 1, 100 ml of p-xylene (799 mmol) and 1 ml of γ-butyrolactone (14.8 mmol) were reacted at 196° C. for 3 hours to obtain 5,8-dimethyltetralone (yield based on γ-butyrolactone: 30.4%). After removing the supernatant by filtration, 100 ml of p-xylene (799 mmol) and 1 ml of γ-butyrolactone (14.8 mmol) as raw materials were charged again and then reacted at 196° C. for 3 hours. As a result, 5,8-dimethyltetralone (yield based on γ-butyrolactone: 23.2%) was obtained. The catalyst could be reused.

Example 3

Reuse and Regeneration of Catalyst

After the completion of the first reaction in Example 1, the supernatant was removed, the remained catalyst was washed with 100 ml of hexane with stirring at room temperature. The hexane supernatant was removed, followed by drying under reduced pressure at 50° C. 100 ml of p-xylene (799 mmol) and 1 ml of γ-butyrolactone (14.8 mmol) as raw materials were charged again and then reacted at 196° C. for 3 hours. As a result, 5,8-dimethyltetralone (yield based on γ-butyrolactone: 28.7%) was obtained. The effect of regenerating the catalyst was exerted.

Example 4

Catalyst Carrying no Tungstosilicic Acid, p-xylene

In the same manner as in Example 1, except that the same amount of tungstosilicic acid (0.320 g) was used in the catalyst in place of 3.20 g of the 10 wt % HSiW/SiO$_2$ catalyst (0.097 mmol-HSiW) used in Example 1, the reaction and analysis were conducted. After the reaction was conducted for 5 hours, the conversion ratio of γ-butyrolactone was 9.0% and the yield of 5,8-dimethyltetralone based on γ-butyrolactone was 2.5. Although the reaction can be conducted even when using the catalyst carrying no tungstosilicic acid, more remarkable effect is exerted using a tungstosilicic acid-carrying catalyst.

Example 5

Silica-carried 10% Phosphotungstic Acid Catalyst, p-xylene

In the same manner as in Example 1, except that 2.90 g of a silica-carried phosphotungstic acid catalyst (manufactured by Wako Pure Chemicals Industries, Ltd., special grade) was used in place of 3.20 g of the 10 wt % HSiW/SiO$_2$ catalyst (0.097 mmol-HSiW) used in Example 1, the reaction and analysis were conducted. After the reaction was conducted for 5 hours, the conversion ratio of γ-butyrolactone was 31.7% and the yield of 5,8-dimethyltetralone based on γ-butyrolactone was 14.1%. The reaction can be conducted even when using a phosphotungstic acid-carrying catalyst.

Example 6

Silica-carried 50% Tungstosilicic Acid Catalyst, p-xylene

In the same manner as in Example 1, except that 3.2 g of a silica-carried 50% tungstosilicic acid catalyst was used in place of 3.20 g of the 10 wt % HSiW/SiO$_2$ catalyst (0.097 mmol-HSiW) used in Example 1, the reaction and analysis were conducted. After the reaction was conducted for 5 hours, the conversion ratio of γ-butyrolactone was 100% and the yield of 5,8-dimethyltetralone based on γ-butyrolactone was 7.4%. Although the reaction can be conducted even when using a 50% tungstosilicic acid-carrying catalyst, the yield is lowered.

Example 7

Silica-carried 25% Tungstosilicic Acid Catalyst, p-xylene

In the same manner as in Example 1, except that 1.6 g of a silica-carried 25% tungstosilicic acid catalyst was used in place of 3.20 g of the 10 wt % HSiW/SiO$_2$ catalyst (0.097 mmol-HSiW) used in Example 1 and a half amount of γ-butyrolactone were used and then the reaction was conducted at a reaction temperature of 210° C., the reaction and analysis were conducted. After the reaction was conducted for 2 hours, the conversion ratio of γ-butyrolactone was 80.8% and the yield of 5,8-dimethyltetralone based on γ-butyrolactone was 67.9%. The yield was higher when using a 25% tungstosilicic acid-carrying catalyst.

Example 8

Catalyst Produced by Using Silica Carrier Containing 1% by Weight of Al

The silica carrier used in Example 1 was impregnated with aluminum nitrate so that it contains 1% by weight of Al, followed by air drying and further sintering at 500° C. for 5 hours to produce a 10 wt % HSiW/SiO$_2$ catalyst in the same manner as in Example 1.

The catalyst thus produced was evaluated in the same manner as in Example 1. As a result, the conversion ratio of γ-butyrolactone was 5.3% and the yield of 5,8-dimethyltetralone based on γ-butyrolactone was 2.4%. As a result of the use of the silica carrier containing 1% by weight of Al, the purity of the carrier purity was 98.9% or higher and a remarkable inhibition effect was exerted, however, a product was obtained.

Example 9

Mesitylene

In the same 100 ml autoclave as in Example 1, 1.5 g of tungstosilicic acid, 40 ml of mesitylene and 2.55 ml of γ-butyrolactone were charged and reacted at 180° C. for 6 hours, and then analysis was conducted. As a result, the conversion ratio of γ-butyrolactone was 85.1% and 2,4,6-trimethylphenylbutyric acid (yield based on γ-butyrolactone: 33.5%) was obtained.

Result

The use of the production process of the present invention makes it possible to synthesize tetralones and indanones in one step reaction, easily recover a catalyst and reuse the catalyst. The present invention exerts large effects such as reduction of wastes, simplification of the separation step and elimination of the use of a reactor made of a high-quality material.

The invention claimed is:

1. A process for producing an aromatic compound by Friedel-Crafts reaction, which comprises reacting an aromatic compound having at least one hydrogen atom attached directly to the aromatic group with an ester compound in the presence of a heteropolyacid-containing solid acid catalyst, wherein the aromatic compound by Friedel-Crafts reaction comprises aromatic ketones, aromatic carboxylic acids, aromatic alcohols, or alkylated or alkenylated aromatics.

2. The process according to claim 1, wherein the heteropolyacid-containing solid acid catalyst is a solid acid catalyst comprising a carrier and a heteropolyacid carried on the carrier.

3. The process according to claim 1, wherein a central atom of the heteropolyacid is selected from the group consisting of P, Si, B, Ge and As and a coordinating atom comprises at least one of Mo and W.

4. The process according to claim 1, wherein a central atom of the heteropolyacid is selected from the group consisting of Si and Ge and a coordinating atom comprises at least one of Mo and W.

5. The process product according to claim 1, wherein an amount of the heteropolyacid carried in the heteropolyacid-containing solid acid catalyst is 50% by weight or less.

6. The process according to claim 1, wherein an amount of the heteropolyacid carried in the heteropolyacid-containing solid acid catalyst is 30% by weight or less.

7. The process according to claim 2, wherein a relative surface area of the carrier supporting the heteropolyacid is 20 m$^2$/g or more.

8. The process according to claim 2, wherein the carrier carrying the heteropolyacid has a purity of 98% or higher.

9. The process according to claim 1, wherein the ester compound comprises lactones.

10. The process according to claim 1, wherein the aromatic compound by Friedel-Crafts reaction is aromatic ketones or aromatic carboxylic acids.

11. The process according to claim 10, wherein the aromatic compound by Friedel-Crafts is aromatic ketones.

12. The process according to claim 1, wherein the Friedel-Crafts reaction product is cyclized ketones.

13. The process according to claim 1, further comprising the step of reusing the heteropolyacid-containing solid acid catalyst after separating and recovering it.

14. The process according to claim 13, wherein the catalyst is regenerated in the step of reusing the heteropolyacid-containing solid acid catalyst after separating and recovering it.

* * * * *